United States Patent
Maniga

(10) Patent No.: US 12,060,178 B2
(45) Date of Patent: *Aug. 13, 2024

(54) CARBON DIOXIDE SHAMPOO APPARATUS AND METHOD OF USE THEREOF

(71) Applicant: Nyangenya Maniga, Litchfield Park, AZ (US)

(72) Inventor: Nyangenya Maniga, Litchfield Park, AZ (US)

(*) Notice: Subject to any disclaimer, the term of this patent is extended or adjusted under 35 U.S.C. 154(b) by 210 days.

This patent is subject to a terminal disclaimer.

(21) Appl. No.: 17/712,583

(22) Filed: Apr. 4, 2022

(65) Prior Publication Data

US 2023/0303279 A1    Sep. 28, 2023

Related U.S. Application Data

(63) Continuation-in-part of application No. 17/709,099, filed on Mar. 30, 2022, which is a continuation-in-part of application No. 17/706,502, filed on Mar. 28, 2022.

(51) Int. Cl.

| | |
|---|---|
| B65B 31/00 | (2006.01) |
| A61K 8/04 | (2006.01) |
| A61K 8/19 | (2006.01) |
| A61K 8/49 | (2006.01) |
| A61Q 5/02 | (2006.01) |

(52) U.S. Cl.
CPC ......... B65B 31/003 (2013.01); A61K 8/046 (2013.01); A61K 8/19 (2013.01); A61K 8/4913 (2013.01); A61K 8/4953 (2013.01); A61Q 5/02 (2013.01); *A61K 2800/22* (2013.01); *A61K 2800/5922* (2013.01)

(58) Field of Classification Search
USPC ................................................... 222/402.1
See application file for complete search history.

(56) References Cited

U.S. PATENT DOCUMENTS

| | | | | |
|---|---|---|---|---|
| 3,810,478 | A | * 5/1974 | Olson, Jr. | ......... C11D 17/0017 |
| | | | | 132/202 |
| 4,685,597 | A | * 8/1987 | Hirao | .................... B65D 83/64 |
| | | | | 222/387 |
| 9,938,072 | B2 | * 4/2018 | Nicmanis | ............. B05B 7/0025 |

(Continued)

FOREIGN PATENT DOCUMENTS

| | | | | |
|---|---|---|---|---|
| WO | WO-2015006408 A1 | * 1/2015 | ............ | A61K 8/046 |

*Primary Examiner* — Paul R Durand
*Assistant Examiner* — Michael J. Melaragno
(74) *Attorney, Agent, or Firm* — Kevin H. Hazen; Hazen Patent Group, LLC

(57) ABSTRACT

The invention comprises a method of making and/or using a shampoo, comprising the steps of: placing shampoo into a container; combining a carbon dioxide precursor with the shampoo; sealing the container to yield a sealed container; and forming carbon dioxide inside the sealed container from the carbon dioxide precursor, the carbon dioxide formed in the sealed container comprising a concentration of greater than one thousand parts per million. Optionally and preferably, the sealed container includes a finger operated valve to release the shampoo from the container and at least one of a carbonic acid, a bicarbonate, and/or a carbonate as the carbon dioxide precursor, where a reaction forms at least one-half of dissolved carbon dioxide in the sealed container.

20 Claims, 6 Drawing Sheets

(56) References Cited

U.S. PATENT DOCUMENTS

| | | | | |
|---|---|---|---|---|
| 2011/0152243 | A1* | 6/2011 | Wishart | C07D 498/04 |
| | | | | 514/249 |
| 2015/0360853 | A1* | 12/2015 | Nicmanis | B65D 83/32 |
| | | | | 222/1 |
| 2023/0301997 | A1* | 9/2023 | Maniga | B65D 83/20 |
| 2023/0302303 | A1* | 9/2023 | Maniga | A61K 9/0014 |
| 2023/0303279 | A1* | 9/2023 | Maniga | A61K 8/44 |

* cited by examiner

CARBON DIOXIDE SHAMPOO APPARATUS AND METHOD OF USE THEREOF

CROSS-REFERENCES TO RELATED APPLICATIONS

This application is a continuation-in-part of U.S. patent application Ser. No. 17/709,099 filed Mar. 30, 2022, which is a continuation-in-part of U.S. patent application Ser. No. 17/706,502 filed Mar. 28, 2022, all of which are incorporated herein in its entirety by this reference thereto.

BACKGROUND OF THE INVENTION

Field of the Invention

The present invention relates to carbon dioxide shampoo in a pressurized container, such as an aerosol container.

Description of Related Art

There are many challenges in the topical application of a shampoo. One major objective is to achieve percutaneous penetration of the active agent to the site of treatment. It is also desirable for the composition to have desirable cosmetic characteristics, for easy and smooth application, and for administration without a noticeable residue on the surface of the skin. It is further desirable that the composition not cause irritation or discomfort. It is still further desirable that application is convenient in terms of time requirements and in terms of necessary clean-up after application.

Aerosol containers are in widespread use as liquid dispensing devices. However, traditional aerosol containers require the use of a pressure container and a toxic and/or environmentally hazardous propellant fluid to create foam. Propellants provide the appropriate vapor pressure within aerosol containers for the expulsion of the formulation as a spray or semisolid when the valve is opened. Typical propellants include liquefied petroleum gases; such as mixture of propane, isobutene, and n-butane; chlorofluorocarbons; methyl ethyl ether; and dimethyl ether, which are flammable, harmful and toxic volatile organic compounds. Further, it is known that the propellant fluid frequently constitutes a source of environmental pollution and sometimes the aerosol container represents a hazard when disposed of since the propellant material are explosive or flammable. Generally, chlorofluorocarbons are banned from use due to their ozone depletion effect, liquefied petroleum gases are flammable, and other propellants such as nitrous oxide may have physiological effects.

Problem

There remains in the art a need for an effective shampoo.

SUMMARY OF THE INVENTION

The invention comprises a pressurized carbon dioxide shampoo.

BRIEF DESCRIPTION OF THE DRAWINGS

A more complete understanding of the present invention is derived by referring to the detailed description and claims when considered in connection with the Figures, wherein like reference numbers refer to similar items throughout the Figures.

DETAILED DESCRIPTION OF THE INVENTION

The invention comprises a method of making and/or using a shampoo, comprising the steps of: placing shampoo into a container; combining a carbon dioxide precursor with the shampoo; sealing the container to yield a sealed container; and forming carbon dioxide inside the sealed container from the carbon dioxide precursor, the carbon dioxide formed in the sealed container comprising a concentration of greater than one thousand parts per million. Optionally and preferably, the sealed container includes a finger operated valve to release the shampoo from the container and at least one of a carbonic acid, a bicarbonate, and/or a carbonate as the carbon dioxide precursor, where a reaction forms at least one-half of dissolved carbon dioxide in the sealed container.

Herein, a z-axis is aligned with gravity, where an x-axis and a y-axis form a plane perpendicular to the z-axis.

Figure 1:
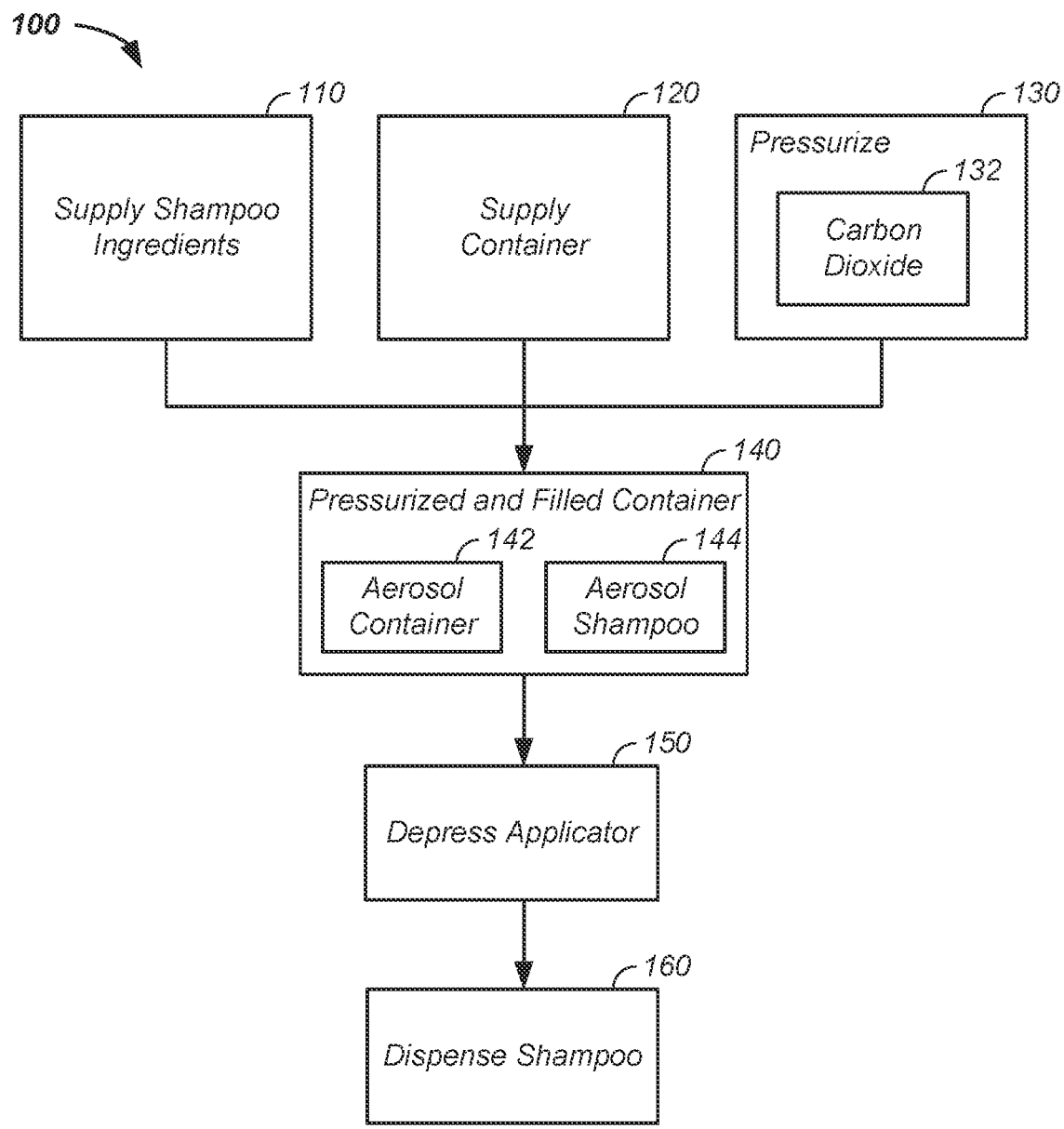
FIG. 1 illustrates packaging and use of an aerosol shampoo.

Referring now to FIG. 1, a method of packaging into a pressurized container and dispensing 100 an aerosol shampoo 144/aerosol shampoo product from the pressurized container is illustrated, where the pressurized container is optionally and preferably an aerosol container 142. Generally, shampoo ingredients 110 are supplied as is a container 120. The shampoo ingredients 110 are placed into the container 120 and the container 120 is pressurized 130 and sealed. Methods of pressurizing the container 120 are further described, infra. For now, an example of pressuring the container 120 with carbon dioxide 132 in the form of a gas is provided, where any other gas is optionally used in place of or in combination with the carbon dioxide 132. Stated again, herein, for clarity of presentation and without loss of generality, carbon dioxide is used to represent any gas and/or any combination of gases. Carbon dioxide is the preferred gas for additional chemical reasons, described infra. In one method of pressuring the container 120, the carbon dioxide 132 is placed into the shampoo ingredients 110 at pressure, such as in a brite tank. The pressurized shampoo and carbon dioxide mix is then pumped into an aerosol can and sealed, optionally keeping the solution cool to maintain the carbon dioxide pressure. In another method, the carbon dioxide is added to the container 120 at time of sealing, such as in a pressurized environment. A third method, a phase change method 200, of pressuring the container 120 is described infra. Similarly, a fourth method, a chemical pressurization method 300, of pressurizing the container 120 is described infra. With any of the methods, the result is a pressurized and shampoo containing product 140/container. To use the aerosol shampoo 144, an actuator 150, such as an applicator button and/or an applicator lever is depressed, which opens a valve/pathway and dispenses 160 the shampoo.

Herein, without loss of generality and for clarity of presentation, non-limiting examples of the aerosol shampoo 144 are provided. However, it is understood that the aerosol shampoo 144 is representative of any personal cleansing product dispensed from an aerosol can.

Figure 2:
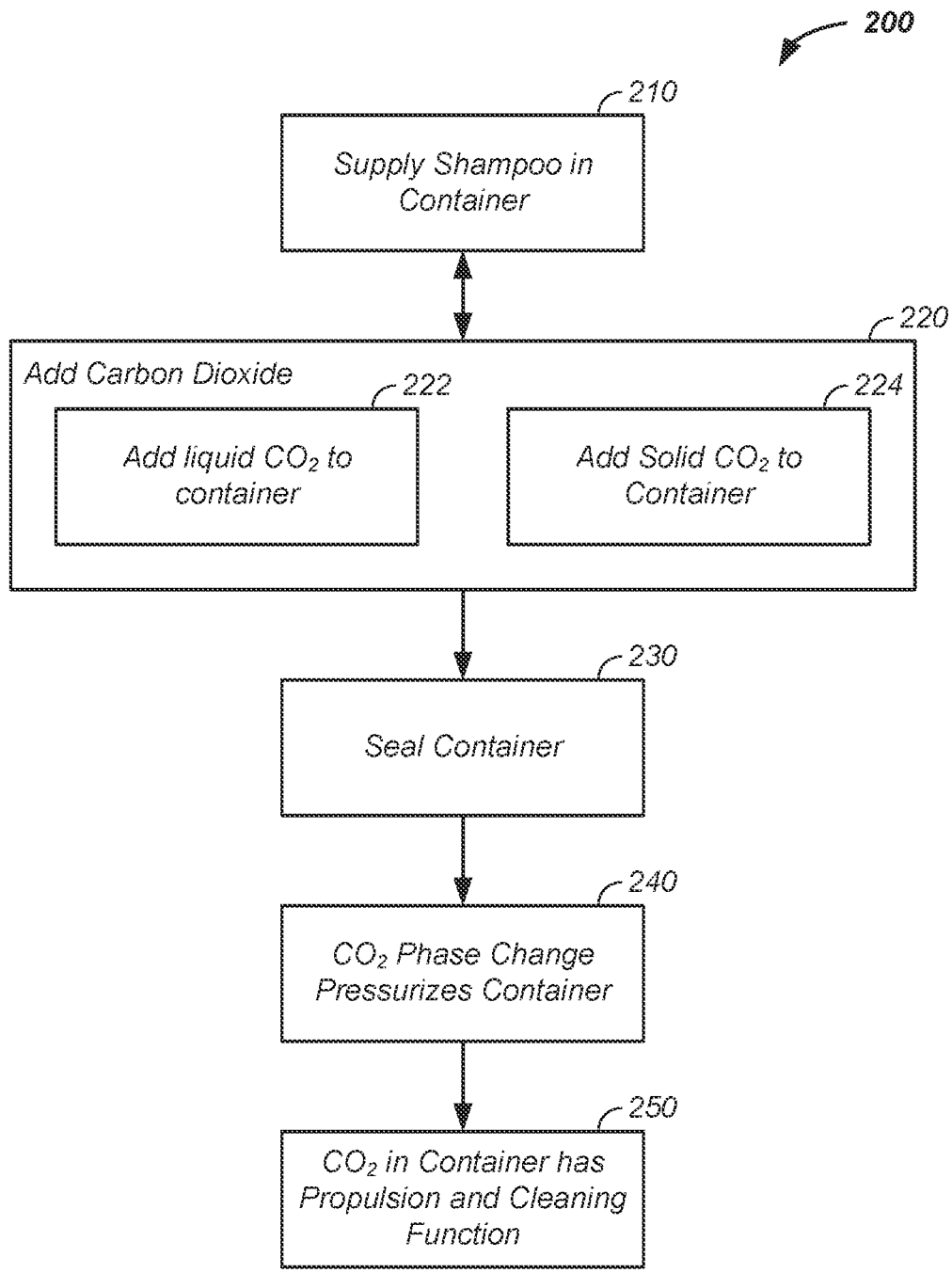
FIG. 2 illustrates pressurizing a container with a solid and/or liquid form of carbon dioxide.

Referring now to FIG. 2, the phase change method 200 is further described. As described, supra, the shampoo ingredients 110 are placed into the container 120 to yield a first step of supplying shampoo in the container 210. In a second step, carbon dioxide is added 220 to the shampoo containing container 210. Optionally, the carbon dioxide 132 is placed into the container 120 and then the shampoo ingredients 110 are placed into the container 120 and/or both components are positioned into the container 120 simultaneously. However, in this phase change method 200, the carbon dioxide 132 is added as a liquid 222 and/or as a solid 224. The container 120 is then sealed 230. Subsequently, the carbon dioxide 132 warms at least 30° C., such as to ambient temperature, and phase changes to a gas phase from the liquid phase and/or the solid phase. As the carbon dioxide 132 undergoes a phase change, the resulting expansion of the carbon dioxide pressurizes 240 the container 120 as the container 120 is sealed 230. Optionally and preferably, the pressure in the aerosol container is raised to the desired pressure of 60 to 200 psi by the expansion of the carbon dioxide. Optionally, additional gas/air is added to the container 120 to bring the pressure up to a specified amount. Naturally, the total increase in pressure is related to the amount of carbon dioxide in a liquid state and/or the amount of carbon dioxide in a solid state added to the container and the total volume of the container, which is readily determined experimentally or calculated by a chemist. Key is that the expansion ratio of carbon dioxide solid to carbon dioxide gas is 782.82:1 at standard temperature and pressure. The ideal gas law (PV=nRT) further relates pressure (P) and volume (V) to the amount of substance of gas (n), the gas constant (R), and absolute temperature (T). For liquid carbon dioxide, a change in pressure related to the initial pressure of the liquid carbon dioxide is required as liquid carbon dioxide only exists at greater than five atmospheres, as seen in a phase diagram of carbon dioxide. Thus, carbon dioxide placed into the shampoo performs two functions 250: (1) bringing the pressure in the container up, which yields a propulsion force and (2) a cleaning function, which is further described infra.

Figure 3:
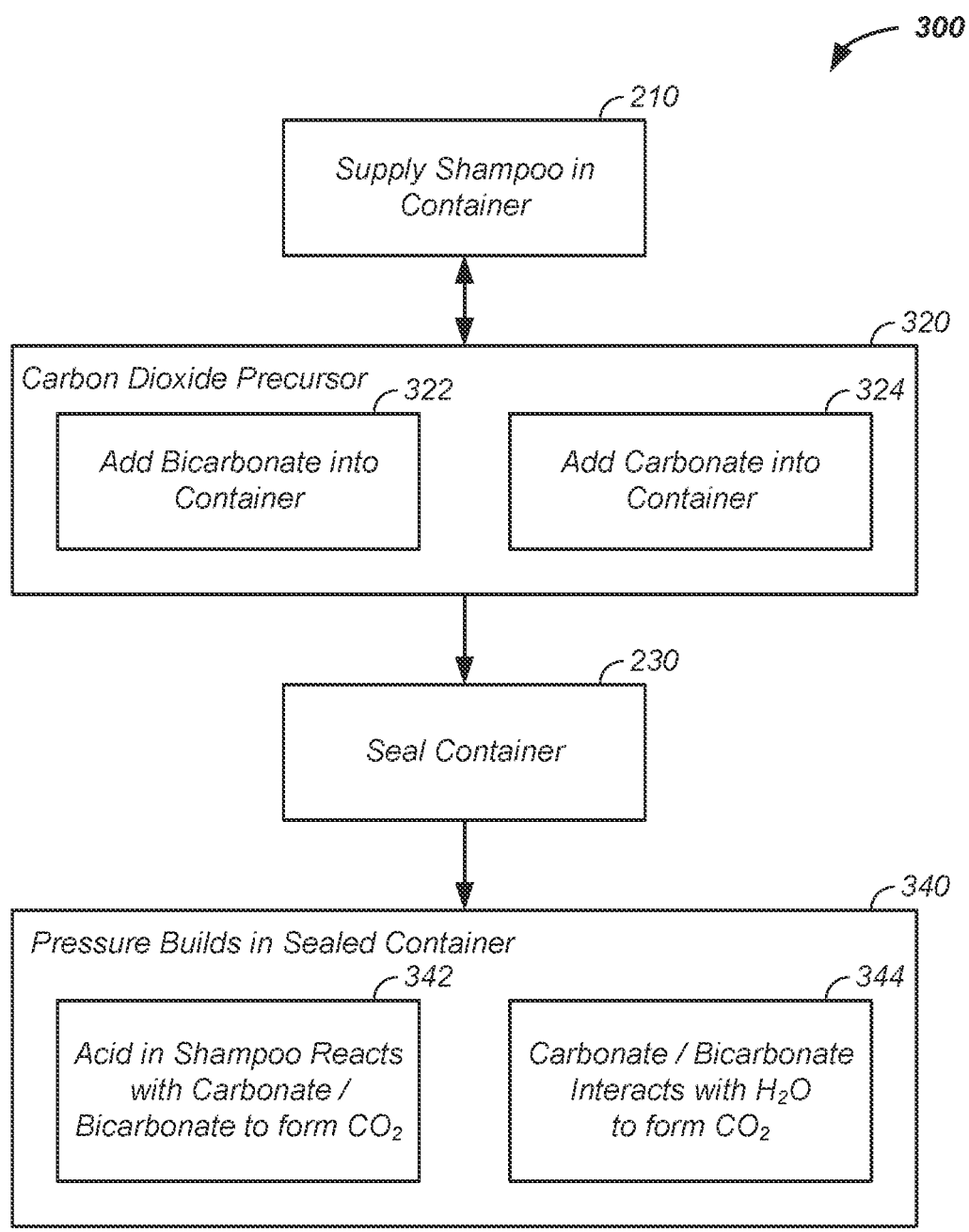
FIG. 3 illustrates forming carbon dioxide in a sealed aerosol container.

Referring now to FIG. 3, the chemical pressurization method 300 is further described. As described, supra, the shampoo ingredients 110 are placed into the container 120 to yield a first step of supplying shampoo in the container 210. In a second step, a carbon dioxide precursor 320 is added 220 to the shampoo containing container 210. Optionally, the carbon dioxide precursor 320 is placed into the container 120 and then the shampoo ingredients 110 are placed into the container 120 and/or both components are positioned into the container 120 simultaneously. In this chemical pressurization method 300, the carbon dioxide precursor 320 yields carbon dioxide as a result of a chemical reaction and/or as a result of an equilibration step. For example, the carbon dioxide precursor 320 is optionally and preferably a carbonate and/or a salt thereof and/or a bicarbonate and/or a salt thereof. The carbon dioxide precursor 320 is optionally in the form of a tablet, resembling an Alka-Seltzer tablet optionally without aspirin and optionally without an acid. Optionally, an acid or any source of a proton, $H^+$, is provided in the shampoo ingredients 110 and/or is added with the carbon dioxide precursor 320, such as in a tablet containing both the carbon dioxide precursor and anhydrous citric acid.

The carbon dioxide precursor 320 and formation of carbon dioxide is further described herein. The carbon dioxide precursor 320 optionally contains at least one of: a carbonic acid, $H_2CO_3$; a bicarbonate, $HCO_3^-$; and/or a carbonate, $CO_3^{2-}$. The bicarbonate and/or the carbonate are optionally in the form of a salt, such as a sodium bicarbonate or a disodium carbonate, where the sodium is optionally any cation, such as $Ca^{2+}$ and $Mg^{2+}$.

Generally, the carbonic acid and bicarbonate are in equilibrium according to equation 1 and the bicarbonate is in equilibrium with the carbon dioxide 132, according to equation 2, where the equilibriums are affected by pH, presence of water, loss of carbon dioxide, and/or temperature.

$$H_2CO_3 \rightarrow HCO_3^- + H^+ \quad \text{(eq. 1)}$$

$$HCO_3^- \rightarrow CO_2(g) + H_2O \quad \text{(eq. 2)}$$

Hence, both the carbonic acid and bicarbonate form carbon dioxide, $CO_2$, in solution as equation 1 leads to a starting reagent of equation 2. The $HCO_3^-$ breaks down quickly to form $CO_2(g) + H_2O$.

Further, in the presence of an acid, either within the shampoo ingredients 110 or added with the carbon dioxide precursor 320, the bicarbonate reacts with the acid to form carbon dioxide, such as through equation 3, where the carbonic acid forms additional bicarbonate, via equation 1, as the bicarbonate concentration decreases in the transformation to the carbon dioxide.

$$HCO_3^- + H^+ \rightarrow CO_2 + H_2O \quad \text{(eq. 3)}$$

For instance, the acidic materials that induce this reaction include, but are not limited to: a hydrogen phosphate, an ionic phosphate, monocalcium phosphate, a phosphate, $H_4P_2O_8$, $CaH_4P_2O_8$, calcium acid phosphate, sodium aluminum phosphate, an amino acid, citric acid, sodium citrate, and/or any source of a proton. Similarly, any acidic component of the shampoo ingredients 110 and/or the carbon dioxide precursor 320 optionally contains the proton, $H^+$, of equation 3, which drives the formation of the carbon dioxide from the carbonic acid and/or the bicarbonate.

Similarly, a carbonate, $CO_3^{2-}$, is simply a salt of carbonic acid, $H_2CO_3$. For instance, calcium carbonate, a salt of carbonic acid, dissociates in solution to form a carbonate, $CO_3^{2-}$, as in equation 4

$$Ca^{2+}CO_3^{2-} \rightarrow CO_3^{2-} + Ca^{2+} \quad \text{(eq. 4)}$$

and the carbonate, $CO_3^{2-}$, is in equilibrium with a bicarbonate, such as in equation 5 and/or is in equilibrium with the carbonic acid, such as in equation 6.

$$CO_3^{2-} + H^+ \rightarrow HCO_3^- \quad \text{(eq. 5)}$$

$$CO_3^{2-} + 2H^+ \rightarrow H_2CO_3^- \quad \text{(eq. 6)}$$

Thus, the carbon dioxide precursor 320 is optionally a carbonate, which yields carbon dioxide, such as in equation 2 optionally driven by equation 1 after forming the carbonic acid and/or the bicarbonate reagents of equations 1 and 2 via equations 6 and 5, respectively.

Thus, if the carbon dioxide precursor contains any carbonate, such as any salt of carbonate, the salt dissolves to form a carbonate that reacts with water to form a bicarbonate, $HCO_3^-$, where the bicarbonate forms carbon dioxide in solution, resulting in the presence of carbon dioxide 132 in the aerosol shampoo. Again, the carbon dioxide has at least two functions 250: (1) bringing the pressure in the container up, which yields a propulsion force and (2) a cleaning function, which is further described infra.

For clarity, it is noted that sodium bicarbonate or sodium hydrogencarbonate, which is commonly known as baking soda or bicarbonate of soda, is a chemical compound with the formula $NaHCO_3$, where the $NaHCO_3$ dissolves in water to form the bicarbonate, $HCO_3^-$, in the above equations.

Similarly, baking powder, is a mixture of: (1) carbonate and/or bicarbonate with (2) a weak acid. Thus, baking soda and/or baking powder provides the reagents, described supra, used to form the carbon dioxide 132 in the aerosol shampoo.

Again, the carbon dioxide precursor 320 is optionally a powder, optionally pressed into a pellet, where the pellet optionally includes an acid, which when dissolved in water provides the acid to react with the carbonate or bicarbonate, as described supra. Said again, the acid of equations 3, 5, and 6 is optionally: provided with the carbon dioxide precursor 320, such is a common tablet, an additional tablet, an additional powder, and/or a liquid and/or the acid is provided by the shampoo ingredients 110. When the acid and carbon dioxide precursor 320 are supplied in a common tablet, the acid and carbon dioxide precursor are optionally and preferably separated by one or more dissolvable components, such as a sugar layer or a flour layer, that dissociates in the water of the shampoo allowing the acid to come into contact with the carbon dioxide precursor 320 to form the carbon dioxide.

Generally, referring again to FIG. 3, the acid, in the shampoo ingredients 110 and/or in the carbon dioxide precursor 320, reacts 342 with the carbonate and/or the bicarbonate to form the carbon dioxide 132 and/or the carbonate and/or the bicarbonate interacts 344 with water to form the carbon dioxide 132, which builds pressure 340 in the sealed container.

Figure 4:
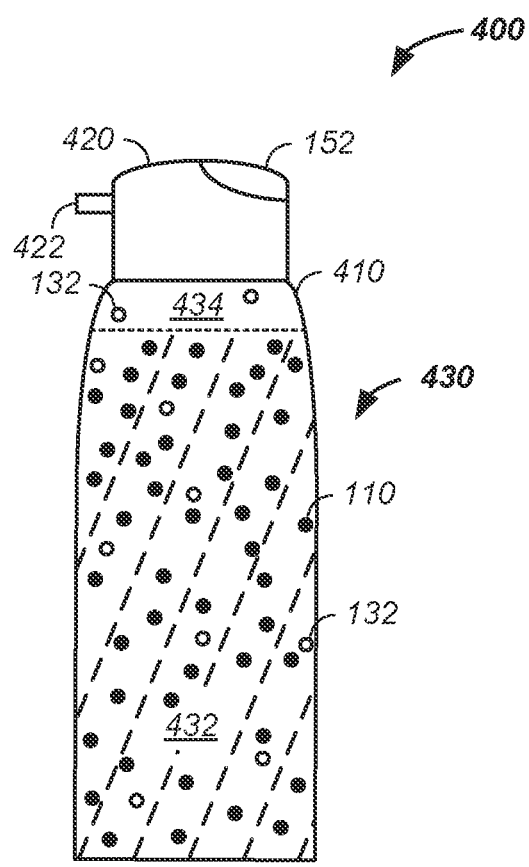
FIG. 4 illustrates an aerosol shampoo.

Referring now to FIG. 4, a carbon dioxide pressurized shampoo product 400 is illustrated. As illustrated, the aerosol container 142 comprises a base container 410 and a cap 420. Optionally and preferably, the cap 420 is crimped onto the base container 210 to form a pressure seal, such as after the solid or liquid carbon dioxide is added to the aerosol container 142 and/or before an air pressure charging step. Optionally and preferably, the actuator is installed onto the can in a separate step. In this example, the actuator 150 is an applicator lever 152, which opens a pathway, via use of a valve, from the aerosol container 142 to a dispensing element 422, such as a stem or aerosol port, which allows passage of the aerosol shampoo 144 from a pressurized volume inside the aerosol container 142 to an ambient pressure/standard atmospheric pressure. Many types of valves exist, such as: toggle, check, globe, plug, gate, globe, plug, ball, butterfly, check, diaphragm, pinch, pressure relief, Lindal, and/or control valves. Herein, all valve types are openable and closable.

Still referring to FIG. 4, the base container 410 holds the shampoo constituents 430, such as the shampoo ingredients 110 and a pressurizing gas. As described, supra, an optional and preferred pressuring gas is carbon dioxide 132 as the carbon dioxide has an additional cleaning role in the shampoo, as further described infra. As illustrated, the shampoo constituents 430 are optionally in a shampoo liquid form 432, which optionally and preferably has a pressurized headspace 434, such as occupied with the carbon dioxide 132 and/or a pressurizing gas. As illustrated, the carbon dioxide 132 is in the pressurized headspace 434. Thus, the carbon dioxide 132 performs a first cleaning function in the shampoo, as described supra, and performs a second function as a propellant, as the pressure in the headspace forces the shampoo constituents 430 out of the base container 410, such as through a dip tube. Notably, the carbon dioxide 132 optionally forms a third function of an expanding agent. More particularly, the carbon dioxide 132 in the shampoo liquid form 432, upon entering the lower pressure environment of ambient pressure, expands, which functions to expand and/or foam the shampoo. A preferred pressure in the shampoo containing container 410 is greater than 10, 20, 50, 100, or 150 psi and less than 300, 250, or 200 psi at time of manufacture. A preferred pressure is 80 psi ±10, 20, 30, 40, 50, 60, or 70 psi. The U.S. Department of Transportation (DOT) carefully regulates the pressure of shipped canisters, such as purchased at a grocery store to contain a maximum pressure of 200 pounds per square inch (psi).

Still referring to FIG. 4, with the carbon dioxide 132 functioning as the propellant, hazardous and/or explosive propellants are not necessary. For example, the carbon dioxide 132 is optionally used to replace or reduce use of a chlorofluorocarbon and/or a fluorocarbon propellant, such as trichloromonofluormethane or dichlorodifluoromethane. Similarly, the carbon dioxide 132 is optionally used to replace or reduce use of a hydrocarbon propellant, such as propane, butane, and/or isobutane. As the carbon dioxide 132 optionally reduces the amount of the propellants by greater than 5, 10, 25, 50, 75, or 99%, the hazards of the container are reduced, which opens up the ability to ship large volumes of the carbon dioxide pressurized shampoo product 400, such as across an international border like the United States—Canadian border, which currently has statutory limits due to the current explosive components. Similarly, by reduction or elimination of the explosive/flammable hydrocarbon propellants, the pressure inside the shampoo containing container 410 is optionally increased beyond the current DOT 200 psi limit, such as to greater than 200, 250, or 300 psi.

Figure 5:
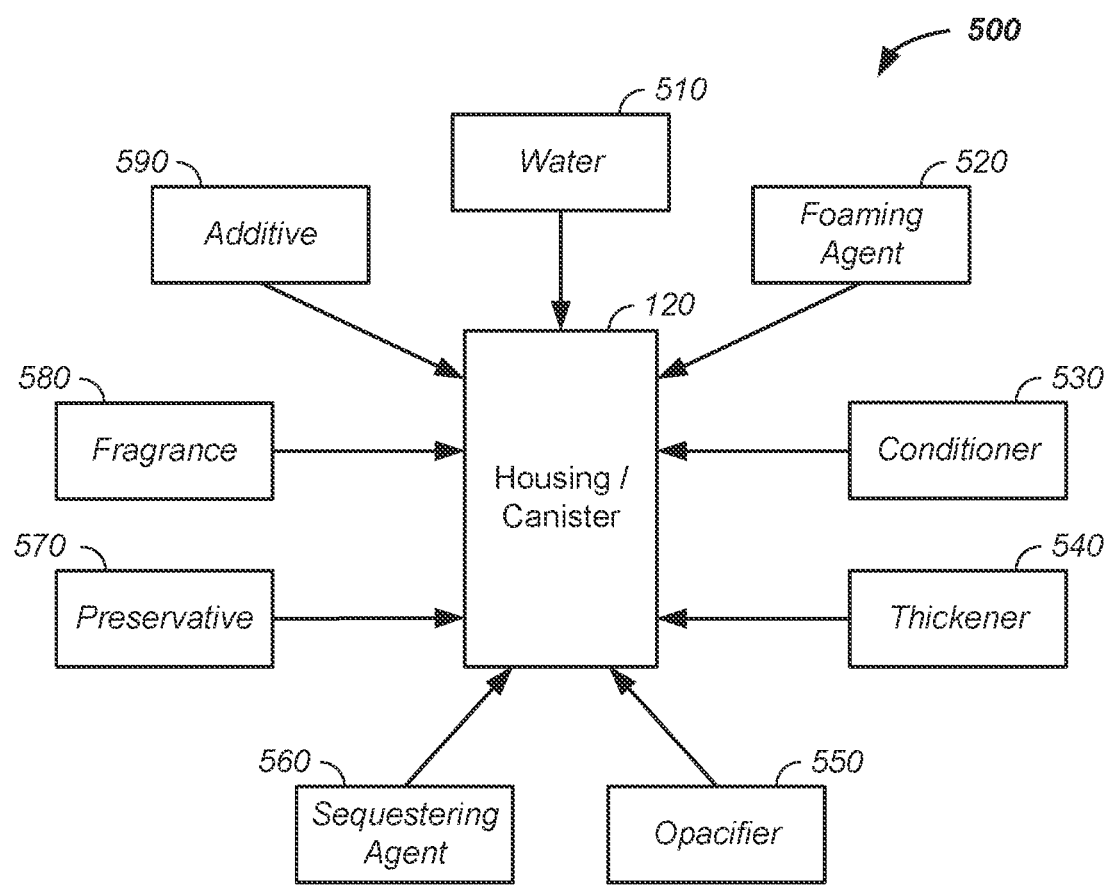
FIG. 5 illustrates shampoo constituents.
Figure 6:
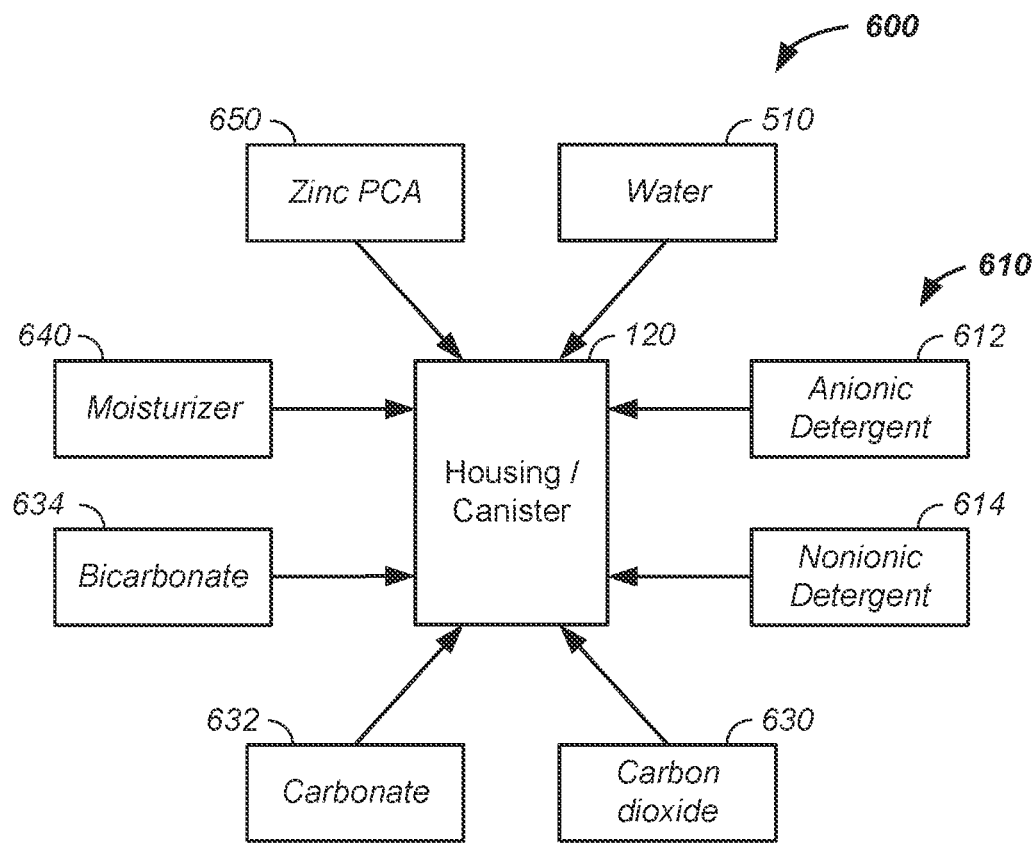
FIG. 6 illustrates a carbon dioxide aerosol shampoo.

Referring now to FIG. 5 and FIG. 6, optional shampoo ingredients 500 are described. Many shampoos are formulated with a few to thirty different ingredients. Water 510, is a common shampoo ingredient and water 510 often makes up a filling constituent, such as to be quantity sufficient and/or to fill up the container and/or to bring other components to a desired concentration. Typically, a shampoo includes a cleansing agent 610, such as an anionic detergent 612, a non-ionic detergent 614, and/or a surfactant. The cleansing agent 610 sufficiently rids the scalp of oil, dirt, sebum buildup, and/or odor by lifting impurities from the scalp, where the impurities are then washed away by water. Examples of detergents in shampoo include: sodium lauryl sarcosinate, sodium lauryl sulfate (SLS), sodium laureth sulfate (SLES), and/or and cocamidopropyl betaine. Additional examples of cleansing agents 610 include: (1) sulfate-free ingredients, such as: sarcosines, sulfosuccinates anionic detergents, betaines, sultaines, and/or imidazolinium and/or a derivative thereof and/or (2) a sulfate-free cleansing agent, such as: sodium lauryl sulfoacetate (SLSA), sodium cocoyl glycinate, sodium cocoyl glutamate, disodium, sodium lauroyl methyl isethionate, sodium lauroyl taurate, sodium lauroamphoacetate, decyl glucoside, and/or lauryl glucoside. Additional shampoo ingredients 500 include: a foaming agent 520, a conditioner 530, a thickener 540, an opacifier 550, a sequestering agent 560, a preservative 570, a fragrance 580, and/or an additive 590. Examples of thickeners 540 include: cetyl alcohol, stearyl alcohol, carnauba wax, xanthan gum, gelatin, cocamidopropyl betaine, and/or stearic acid. Examples of sequestering agents 560 that prevent scum from forming on hair include: polyphosphates and/or ethylenediaminetetraacetic acid. The preservatives 570, which function to prevent bacteria formation, include: sodium benzoate, 1,3-dimethylol-5,5-dimethyl (DMDM) hydantoin, tetrasodium EDTA, methylisothiazolinone, potassium sorbate, sorbic acid, dehydroacetic acid, and/or benzyl alcohol. Examples of additives 590, include: a vitamin, panthenol, an essential oil, fruit extracts, botanicals, plant oils, such as jojoba oil, geranium, and argan oil, organic green tea, aloe, chamomile, coconut oil, organic honey, bergamot essentials oils, olive, organic hemp, root extracts, such as burdock root, fruit extracts, such as star anise, essential oils, such as peppermint, lavender, and lemon, and/or the moisture-retaining humectant glycol. Shampoo is optionally pH balanced, such as with citric acid and/or glycolic acid.

Referring now to FIG. 6, a pressurized and hydrated carbon dioxide shampoo 600 is described. Pressurized and hydrated carbon dioxide has cleaning properties. For instance, when under pressure, carbon dioxide 132 is used as a solvent of organic compounds. Further, when under pressure, carbon dioxide 132 protonates the hydrogen bicarbonate anion, which aids in extraction of organic compounds. Similarly, if carbon dioxide 132 is incorporated with other cleansing agents 610, such as the anion detergent 612 and/or the nonionic detergent 614, carbon dioxide 132 aids in the removal of oils on the scalp secreted by the sebaceous glands effectively achieving a cleaning action, such as by solvation. In one example, bicarbonate is used as a dry shampoo. When applied to the scalp, the bicarbonate reacts with sebacic acid and makes it partially soluble in an aqueous solution, which ultimately aids in washing off sebacic acid. Generally, the $HCO_3^-$ reacts with sebacic acid to form sebacate and bi-products, such as carbon dioxide, optionally in the presence of an acid, $H^+$. Sebacate is a conjugate base of sebacic acid.

Example I

In a first example, carbon dioxide 132 is packaged in an aerosol container at a concentration of greater than 4000, 5000, 6000, 8000, or 10,000 ppm and/or at a concentration of less than 100,000 ppm. Optionally and preferably, the carbon dioxide 132 is packaged in the aerosol container with at least 0, 1, 2, 3, or more cleansing agents 610. Even by itself, the carbon dioxide 132, as dry aerosol shampoo, cleanses the hair, takes oils off of the scalp, provides a calming sensation to the scalp, and/or promotes scalp health.

Example II

In a second example, carbon dioxide 132 is packaged in an aerosol container at a concentration of greater than 1000, 2000, 3000, 4000, 5000, 7500, 10,000, 15,000, or 25,000 ppm along with at least one cleansing agent 610.

Example III

In a third example, carbon dioxide 132 is packaged in an aerosol container at a concentration of 5,000 to 100,000 ppm (5000 to 100,000 mg/L) (5 g/L to 100 g/L) or 0.5 to 10% by mass along with at least one cleansing agent 610. One optional cleansing agent 610 is pyrrolidone carboxylic acid (PCA), which is a natural moisturizing factor that helps the skin process hydration and/or energy. The PCA is optionally used as any salt. However, an optional and preferred form of PCA is zinc PCA, where PCA is optionally and preferably L-PCA. A preferred concentration of zinc PCA is 0 to 5% and/or greater than 0.1, 0.25, 0.5, or 1% zinc PCA. A preferred embodiment of the aerosol shampoo also includes moisturizers and water, quantity sufficient.

Example IV

In a fourth example, minoxidil is optionally added to the shampoo. For instance, the shampoo optionally includes more than 0.5, 1, 2, 3, 4, or 5 percent minoxidil, or a pharmaceutically acceptable salt thereof, by weight, based on total weight of the shampoo.

In various production methods, carbon dioxide and water are pumped into an aerosol can at a concentration of 1-2% by mass. Optionally all of the shampoo products are initially mixed and then the carbon dioxide is added, such as in a pressurized can.

Notably, the carbon dioxide 132 is optionally and preferably in an aerosol container/pressurized container as the desired concentration of carbon dioxide 132 is 5,000 to 100,000 ppm to maintain cleansing/solvent properties. If not pressurized, the carbon dioxide 132 is lost from the container, such as a standard shampoo container with a lever opening contents of the container to direct contact with the atmosphere. Stated again, $HCO_3^-$ is in equilibrium with carbon dioxide 132 and water, and as the carbon dioxide 132 bubbles off in a non-pressurized container, the $HCO_3^-$ is quickly lost to atmosphere as carbon dioxide 132 in a non-pressurized container.

Notably, the natural concentration of carbon dioxide in air is 412 ppm. Hence the concentration of at least 5000 ppm carbon dioxide in the shampoo or in the headspace above the shampoos is dramatically higher than a concentration of carbon dioxide in atmosphere. Even at 80 psi, which is five atmospheres of pressure, the carbon dioxide is still only 412 ppm; not 5× or 2060 ppm (412*5).

Still yet another embodiment includes any combination and/or permutation of any of the elements described herein.

Herein, a set of fixed numbers, such as 1, 2, 3, 4, 5, 10, or 20 optionally means at least any number in the set of fixed number and/or less than any number in the set of fixed numbers.

Herein, any number optionally includes a range of numbers such as the number, n, ±1, 2, 3, 4, 5, 10, 20, 25, 50, or 100% of that number.

The particular implementations shown and described are illustrative of the invention and its best mode and are not intended to otherwise limit the scope of the present invention in any way. Indeed, for the sake of brevity, conventional manufacturing, connection, preparation, and other functional aspects of the system may not be described in detail. Furthermore, the connecting lines shown in the various figures are intended to represent exemplary functional relationships and/or physical couplings between the various elements. Many alternative or additional functional relationships or physical connections may be present in a practical system.

In the foregoing description, the invention has been described with reference to specific exemplary embodiments; however, it will be appreciated that various modifications and changes may be made without departing from the scope of the present invention as set forth herein. The description and figures are to be regarded in an illustrative manner, rather than a restrictive one and all such modifications are intended to be included within the scope of the present invention. Accordingly, the scope of the invention should be determined by the generic embodiments described herein and their legal equivalents rather than by merely the specific examples described above. For example, the steps recited in any method or process embodiment may be executed in any order and are not limited to the explicit order presented in the specific examples. Additionally, the components and/or elements recited in any apparatus embodiment may be assembled or otherwise operationally configured in a variety of permutations to produce substantially the same result as the present invention and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. A method, comprising the steps of:
   placing shampoo into a container;
   combining a carbon dioxide precursor with said shampoo;
   sealing said container to yield a sealed container; and
   forming carbon dioxide inside said sealed container from said carbon dioxide precursor, said carbon dioxide formed in said sealed container comprising a concentration of greater than five thousand parts per million.

2. The method of claim 1, said step of sealing further comprising the step of:
   crimping a cap on said container; and
   adding a finger operated valve to said container, said valve configured to release said shampoo to atmosphere.

3. The method of claim 2, said step of combining comprising the step of:
   adding into said container at least one of:
      a carbonic acid at a concentration of greater than one thousand parts per million; and
      a bicarbonate at a concentration of greater than two thousand parts per million.

4. The method of claim 1 said step of combining comprising the step of:
   placing into said container at least one of:
      a form of carbonate at a concentration exceeding 2.5 g/L;
      $CO_3^{2-}$ at a concentration exceeding 2.5 g/L; and
      a salt of carbonic acid at a concentration exceeding 2.5 g/L.

5. The method of claim 1, said step of forming further comprising the step of:
   chemically generating, via a chemical reaction, said carbon dioxide with a chemical reagent, said chemical reagent comprising said carbon dioxide precursor.

6. The method of claim 5, said step of chemically generating further comprising the step of:
   reacting a bicarbonate, $HCO_3^-$, with an acid, $H^+$, to form at least half of said carbon dioxide.

7. The method of claim 6, wherein said acid comprises at least one of:
   a hydrogen phosphate;
   an ionic phosphate;
   monocalcium phosphate;
   a phosphate;
   $H_4P_2O_8$;
   $CaH_4P_2O_8$;
   calcium acid phosphate; and
   sodium aluminum phosphate.

8. The method of claim 6, wherein said acid comprises at least one of:
   an amino acid;
   citric acid; and
   sodium citrate.

9. The method of claim 6, wherein said acid comprises:
   a proton source.

10. The method of claim 5, said step of chemically generating further comprising the step of:
    dissociating a salt of carbonic acid to form a carbonate.

11. The method of claim 10, further comprising the step of:
    generating at least half of said carbon dioxide through equilibration with said carbonate.

12. The method of claim 1, further comprising the step of:
    propelling said shampoo from said container with a propulsion force, at least ten percent of said propulsion force from a fraction of said carbon dioxide chemically generated inside said sealed container.

13. The method of claim 1, further comprising the step of:
    propelling said shampoo from said sealed container with a propulsion force, at least ten percent of said propulsion force from a fraction of said carbon dioxide chemically generated inside said sealed container and at least one percent of said propulsion force from a fraction of said carbon dioxide generated through a phase change of at least one of a solid and a liquid to a dissolved gas form of said carbon dioxide.

14. The method of claim 13, further comprising the step of:
    cleaning hair with said carbon dioxide once dispersed from said container.

15. The method of claim 13, further comprising the step of:
    solvating sebacic acid, with said carbon dioxide, as a function of said shampoo once dispensed from said container.

16. The method of claim 1, further comprising the step of:
    foaming said shampoo through an expansive force of said carbon dioxide going from a pressurized environment inside said sealed container to an atmospheric pressure.

17. The method of claim 1, further comprising the step of:
    distributing zinc pyrrolidone carboxylic acid in said shampoo.

18. The method of claim 1, further comprising the step of:
    combining minoxidil with said shampoo, said minoxidil comprising greater than one tenth of a percent minoxidil by mass of said shampoo.

19. The method of claim 1, further comprising the steps of:

pressurizing said container with a pressure exceeding ten pounds per square inch, at least one-half of said pressure from said carbon dioxide formed in said container; and cleaning hair with said carbon dioxide within thirty seconds of dispensing said shampoo from said container.

20. The method of claim 1, further comprising the steps of:

expelling with a propulsion force said shampoo from said container to atmosphere, at least ten percent of said propulsion force from said carbon dioxide; and said carbon dioxide functioning as a cleansing agent of hair once dispersed from said container.

* * * * *